United States Patent [19]
Witzke et al.

[11] Patent Number: 5,332,900
[45] Date of Patent: Jul. 26, 1994

[54] ON-LINE CORROSIVITY MONITOR FOR PETROLEUM PRODUCTS

[75] Inventors: Horst Witzke, Flemington; Joshua Varon, Marlboro, both of N.J.

[73] Assignee: Exxon Research & Engineering Co., Florham Park, N.J.

[21] Appl. No.: 17,588

[22] Filed: Feb. 16, 1993

[51] Int. Cl.⁵ .............. G01N 21/75; G01N 17/00; G01N 33/28
[52] U.S. Cl. ................ 250/341; 250/301; 436/6
[58] Field of Search ............ 250/301, 341; 436/6

[56] References Cited

U.S. PATENT DOCUMENTS

| | | | |
|---|---|---|---|
| 4,209,695 | 6/1980 | Arnold et al. | 250/270 |
| 5,068,196 | 11/1991 | Hays et al. | 436/6 |
| 5,155,555 | 10/1992 | Wetegrove et al. | 356/381 |

FOREIGN PATENT DOCUMENTS

| | | | |
|---|---|---|---|
| 57-40652 | 3/1982 | Japan | 436/6 |
| 58-91655 | 5/1983 | Japan | 436/6 |

*Primary Examiner*—Constantine Hannaher
*Attorney, Agent, or Firm*—Ronald D. Hantman

[57] ABSTRACT

A method and system for monitoring the presence of a corrosive constituent in a petroleum product. [The invention detects the reflected] Reflected radiation is detected from a metal standard in the petroleum product which indicates the presence of the corrosivity constituent.

12 Claims, 7 Drawing Sheets

ON-LINE CORROSIVITY MONITOR FOR PETROLEUM PRODUCTS

BACKGROUND OF THE INVENTION

The corrosion of metal equipment by petroleum products is controlled by limiting the corrosivity of the product. In practice, either the level of certain impurities is specified or the degree of corrosion of a specific metal which is allowable under standardized test conditions is specified. The Copper Strip Corrosion Test is such an example. Copper is chosen because it is the most corrosion sensitive metal to be encountered by most petroleum products. In many cases sulfur containing species such as hydrogen sulfide, mercaptans, organic sulfides, carbonyl sulfide and even elemental sulfur are of prime concern.

In the case of the Copper Strip Corrosion Test for liquefied petroleum gas (LPG), a freshly polished piece of copper is immersed in a sealed pressure bomb containing 100 ml of LPG for 1 hour at 38° C. After removal the copper is inspected visually for any tarnish and compared to a standard color chart available from the ASTM. Depending on the degree of tarnish, the LPG is then assigned a grade ranging from 1 to 4, the former indicating essentially no tarnish, and the latter indicating severe tarnish (essentially black). In most situations only grade 1 LPG is used commercially. The exact specifications for this test can be found in ASTM test designation No. D 1838-84. Similar test specifications are available from the ASTM for other products such as Jet fuel, for example.

The test is clearly laborious, time consuming, imprecise and dependent upon an operators visual judgment. Furthermore, the scientific reasons for the formation of the colors listed in the ASTM specification have not been explained before.

It is the purpose of this invention to provide for a method and an instrument to automate and help quantify the Copper Strip Corrosion Test for petroleum products as practiced in a typical refinery laboratory. In addition, it is the purpose of this invention to provide a means for carrying out corrosivity testing on-line as the petroleum product is being produced or shipped via a pipeline, for example.

SUMMARY OF THE INVENTION

The present invention is a method and system for on-line monitoring the corrosivity of a petroleum feedstream for the presence of a corrosive constituent. The method includes the steps of irradiating a metal that reacts with said corrosive constituent, wherein the coupon is installed in said feedstream, detecting the reflected radiation from the metal, converting said reflected radiation to an electrical signal indicative of the magnitude of the reflected radiation, repeating the above steps, and determining a change in the electrical signal and relating it to the corrosivity of said feedstream of the metal. In a preferred embodiment, the first three steps are performed continuously.

The system includes a housing having valves for admitting and releasing a sample of the petroleum feedstream, a source of visible or infra-red light, a metal coupon that reacts with said corrosive constituent, means for irradiating the coupon with the light, a means for detecting the reflected light from the metal coupon, and a means for converting the reflected into an electrical signal which is indicative of the corrosivity of the petroleum product.

DESCRIPTION OF THE PREFERRED EMBODIMENT

The new method and system described in this invention employs a light source and a photodetector and associated electronic equipment to measure and display the signal from the photodetector. Light from the light source is allowed to impinge upon a polished metal surface and the reflected light is allowed to fall upon the photodetector. The signal from the photodetector is recorded on a strip chart recorder or preferably sent to a data acquisition card in a computer as is well known to those skilled in the art. If the metal surface becomes tarnished, the measured reflectivity will generally decrease from the value measured on a freshly polished piece of metal. For many corrosive constituents, copper is a preferred metal.

A preferred embodiment of this invention employs a fiber optic probe, using either a single fiber for both the impinging and reflected light, or separate fibers for the impinging and reflected light. More than one fiber may be used for either function as well. A convenient light source and photodetector combination is manufactured by OMRON (Model No. E3XA-CC4A), Exton, Pa., where the light source is a red light emitting diode (LED).

Example 1

Figure 1:
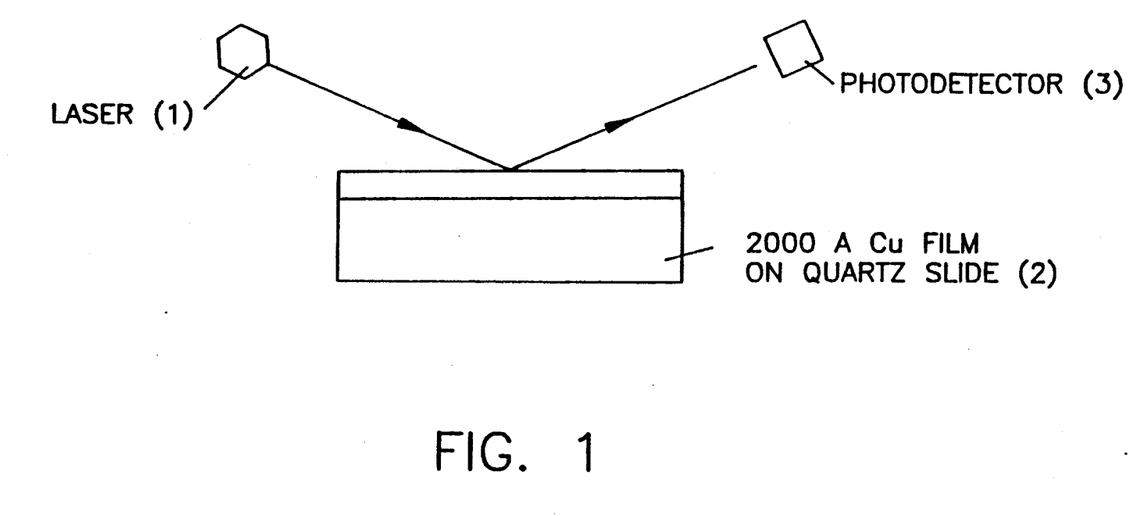
FIG. 1 shows schematically a typical arrangement for the practice of the present invention.
Figure 2:
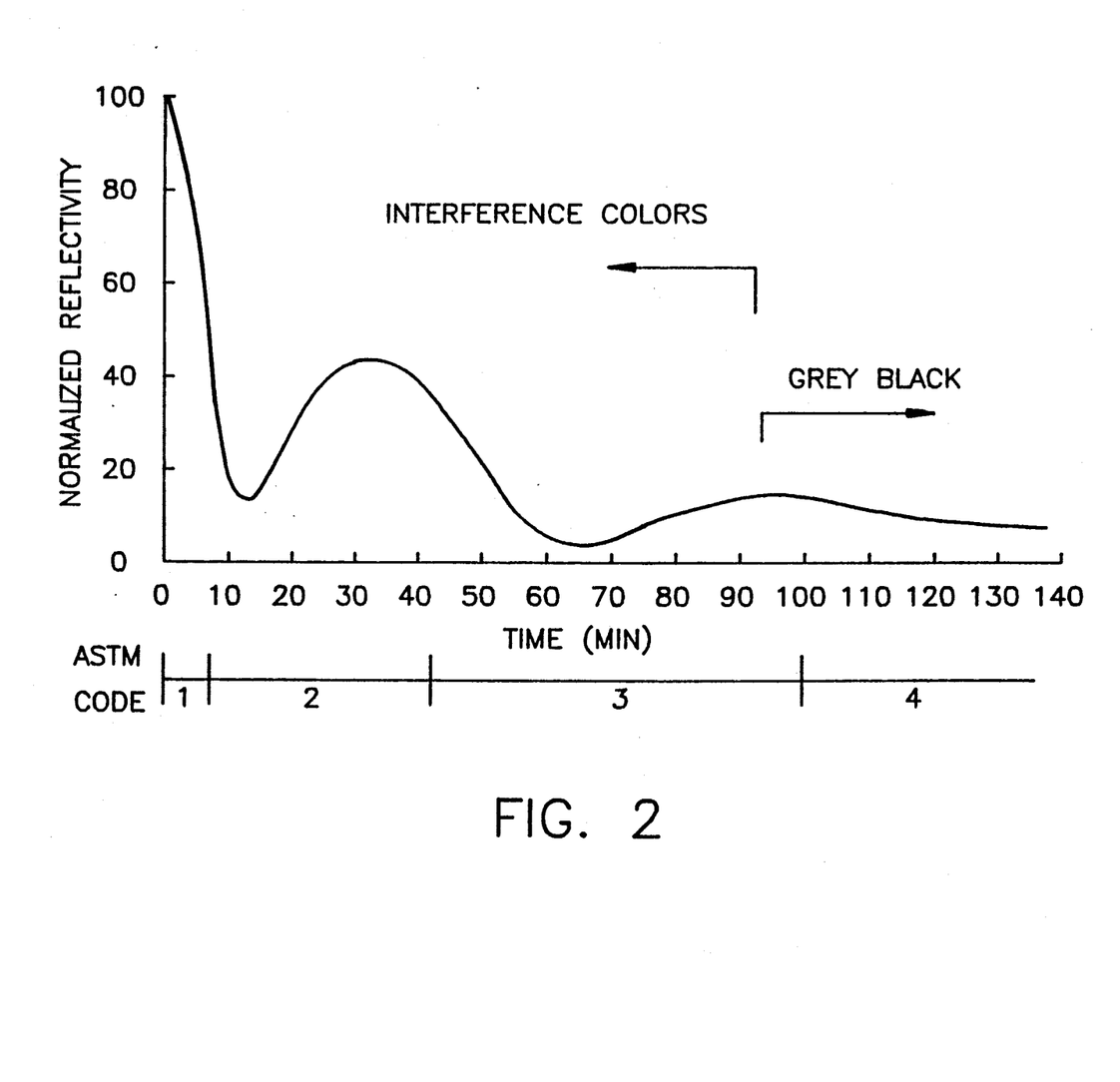
FIG. 2 shows the time evolution of the intensity of the reflected light when the copper sample is exposed to argon gas containing 1000 ppm of hydrogen sulfide at 70° C.

FIG. 1 shows schematically a typical arrangement for the practice of this invention. Light from a helium-neon laser (1) (e.g., Oriel Model No. 79421, Stratford, Conn.) impinges upon a piece of polished copper, a copper coupon, or a thin film of copper deposited on a suitable substrate such as quartz (2). The intensity of the reflected light is measured by a silicon photodetector (3) (e.g., Newport Model No. 818-SL, Fountain Valley, Calif.) with an accompanying voltmeter for example (not shown). Although monochromatic light is used in this example and is the preferred method, a white light source such as a tungsten bulb could also be employed. FIG. 2 shows the time evolution of the intensity of the reflected light, normalized to 100% at the start of the test, when the copper sample is exposed to argon gas containing 1000 ppm of hydrogen sulfide at 70° C. The figure shows that the measured reflectivity at the wavelength of the helium neon laser (6328 A) shows an oscillatory behavior as a function of time. The explanation for this behavior is the formation of a thin, essentially optically transparent film on a reflective surface. Such behavior is known to give rise to optical interference colors and is employed in the manufacture of anti-reflection coatings for photovoltaic solar cells, for example (see, for example, "Non-destructive Determination of Thickness and Refractive Index of Transparent Films", W.A. Pliskin, etal, IBM J. Res. Develop., Vol. 8, pp. 43-51, 1964). In the example shown, the thin film that is formed on the surface of the copper is due to corrosion of the copper by the hydrogen sulfide and the formation of a copper sulfide film. The corrosion rate decreases with time as sulfide film formation becomes diffusion controlled. By carrying out a series of experiments where the copper sample was exposed to a limited time and then removed from the chamber, it has been possible to correlate the measured reflectivity of a corroding copper sample with the ASTM color chart and hence the grade implied by that color. This is shown in the bar at the bottom of FIG. 2. Thus, for the first time, the ASTM color chart for the Copper Strip Corrosion Test has been explained in terms of optical interference colors.

Similar experiments employing methyl mercaptan in argon at elevated temperatures and hydrogen sulfide dissolved in toluene at ambient temperatures gave essentially similar results, i.e., an oscillating reflectivity curve as a function of time of exposure. The major difference observed was that the time axis changed, since the corrosiveness of different sulfur species differs, as is well known. Elemental sulfur dissolved in toluene was also found to readily corrode copper, however, no interference colors were formed. The copper changes from shiny to grey-black. Nevertheless the resulting monotonic decrease in reflectivity can also be detected and measured by the methodology disclosed in this invention. It is therefore now possible to continuously monitor the corrosion of a copper sample under controlled conditions and assign a Copper Strip Test grade to the sample. The test can therefore be made more quantitative than was heretofore possible. In addition, the test can be done in situ by employing optical windows or fiber optic probes. Similar graphs can be obtained for other metal coupons and other corrosive constituents.

EXAMPLE 2

Figure 3:
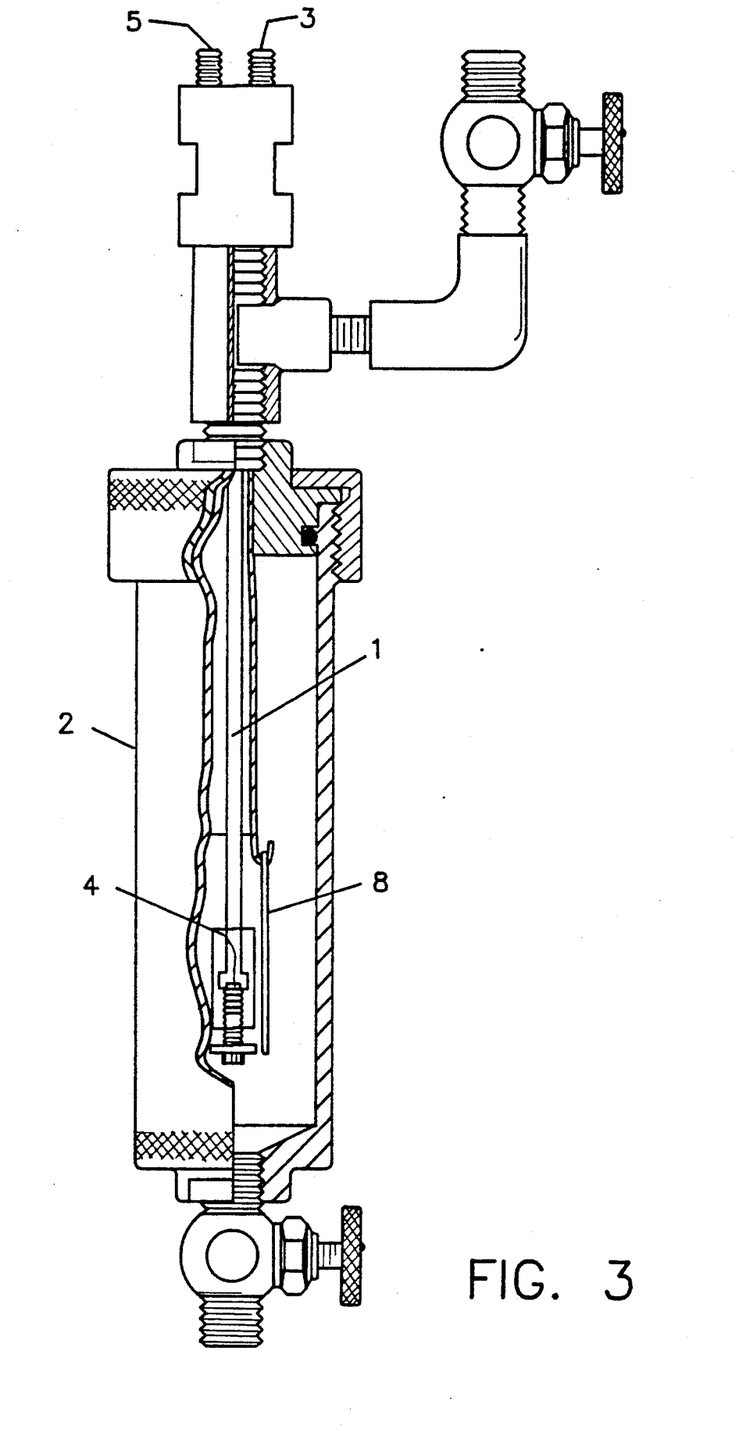
FIG. 3 shows a schematic diagram of the system of the present invention.
Figure 4:
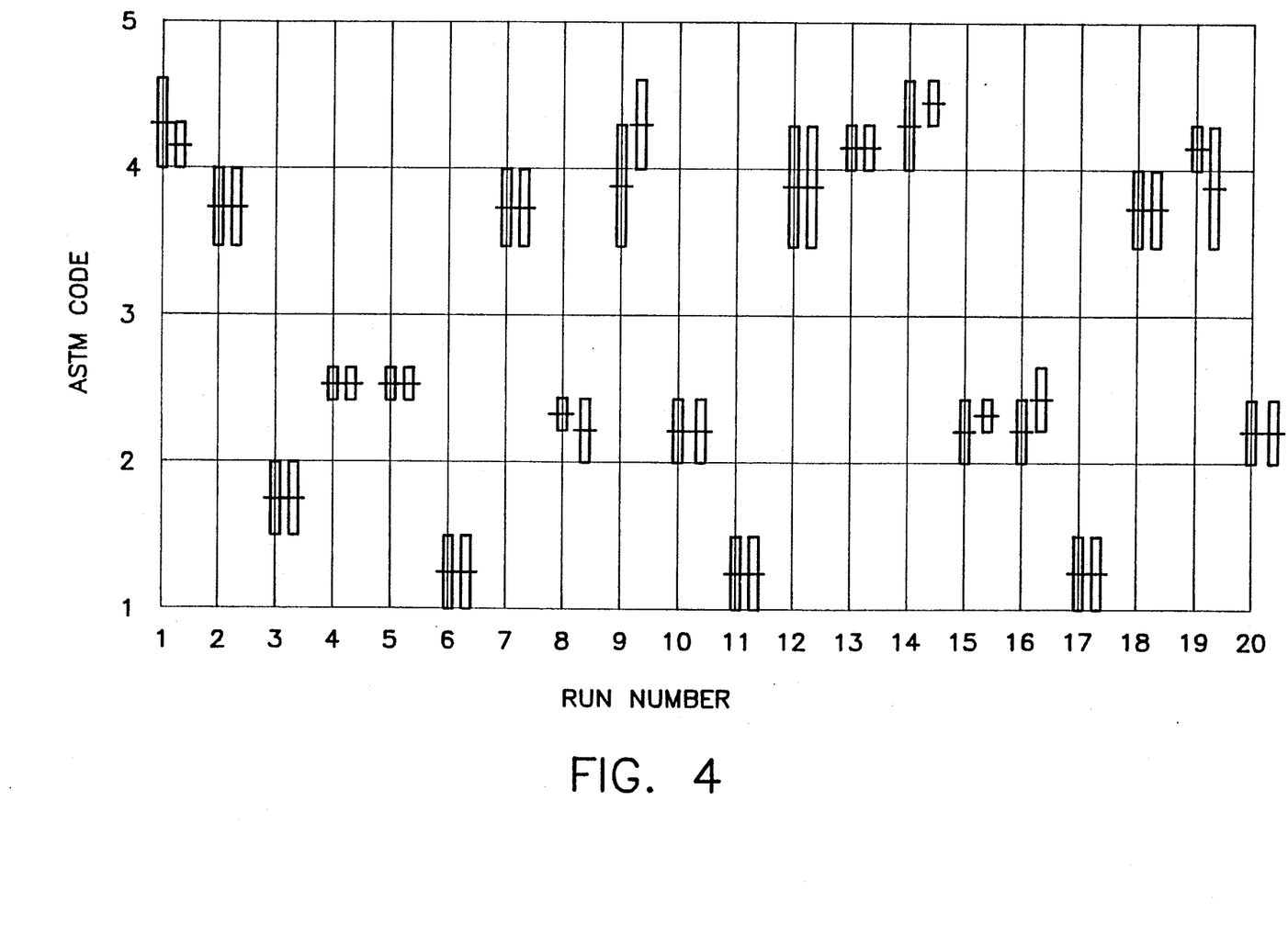
FIG. 4 shows a comparison of a standard ASTM test and the present invention.

The methodology of this invention was tested with LPG in a refinery laboratory using the arrangement shown in FIG. 3. A fiber optic probe (1) was inserted into a standard Copper Strip Corrosion test bomb (2). A small polished piece of copper (4) was placed at the end of the fiber optic probe. A light source (not shown) and photo detector (8), an OMRON E3XA-CC4A module, was employed to monitor the reflectivity of the copper sample. Light entered at (3) and reflected light emerged at (5). A standard ASTM copper coupon was also placed into the bomb. The bomb was then filled with samples of LPG obtained from normal product streams that were known to be non-corrosive, as well as samples from streams that were known to be contaminated with high concentrations of primarily hydrogen sulfide at concentrations up to the 200 ppm level. The standard ASTM test was run and the LPG grade obtained from the fiber optic probe using FIG. 2 was compared to that obtained from the standard test coupon as judged by an experienced refinery laboratory operator. The results of 20 such tests are shown in FIG. 4. For each test, the ASTM grade is shown as two bars. The left bar (crosshatched) is the grade obtained from the standard test coupon, and the right bar is the grade obtained from the fiber optic probe. The length of the bar shows the uncertainty in the measurement. FIG. 4 shows the good agreement obtained and thus validates the methodology disclosed in this invention.

EXAMPLE 3

Figure 5:
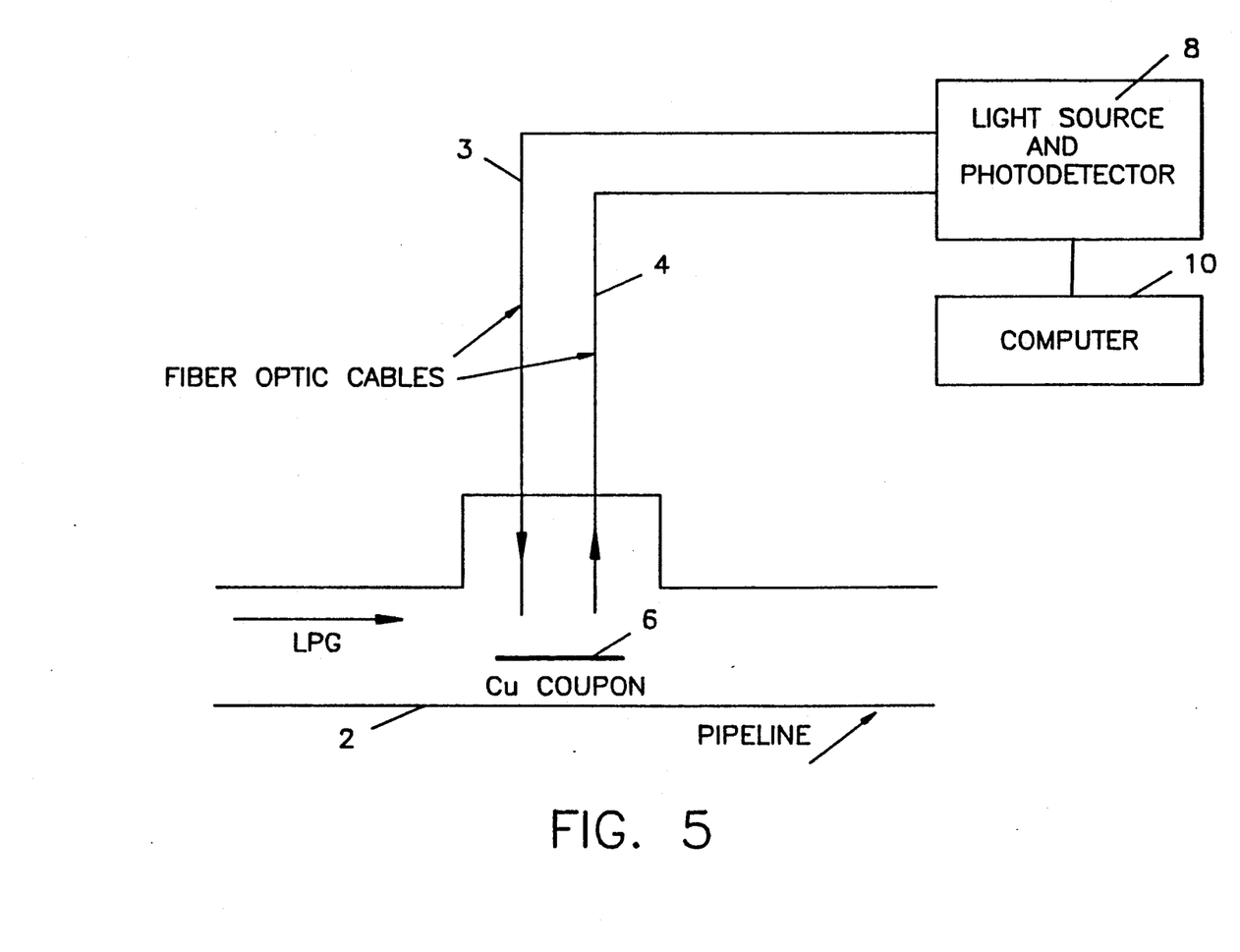
FIG. 5 shows a schematic diagram of the system for on-line monitoring.

The methodology of this invention was tested on-line on product streams in a refinery. The equipment and arrangement is shown schematically in FIG. 5. A fiber optic probe having cables (3) and (4) was inserted into a pipeline. At the end of the fiber optic probe a small piece of polished copper was held in place by a sample holder (6). An OLRON unit 8 as described in Example 2 above was used as the light source and detector. The signal from the OMRON unit was sent continuously to a computer 10 and stored for later data processing. The tests were run under ambient conditions. The petroleum product was allowed to flow continuously past the fiber optic probe, thus continuously exposing the copper coupon to the product stream.

Figure 6:
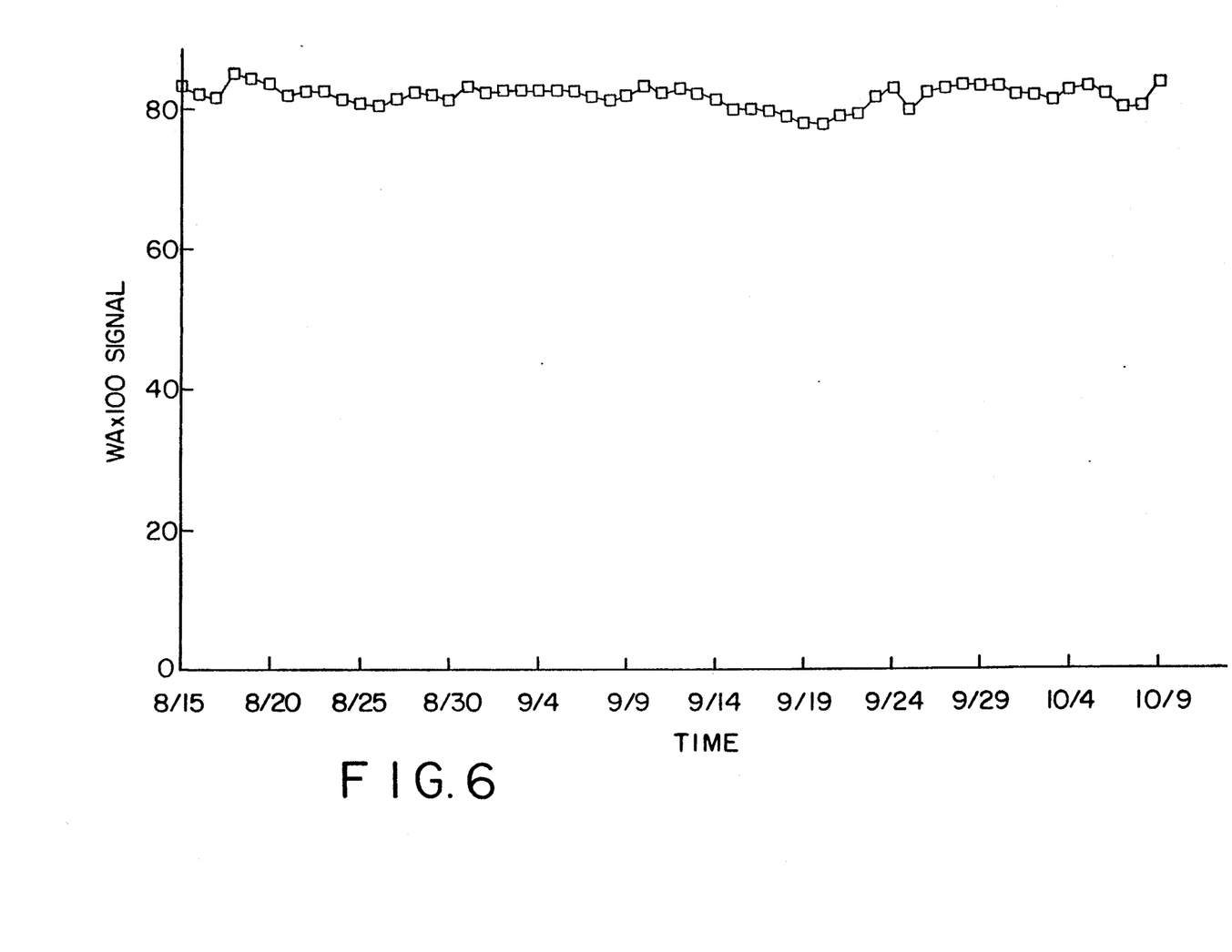
FIG. 6 shows the obtained signal as a function of time for the on-line monitoring of a pipeline carrying natural gas.

FIG. 6 shows the signal obtained from the OMRON unit over several weeks. It was known that the product stream was essentially totally free of any sulfur species and no corrosion of the copper was expected. The signal from the fiber optic probe is seen to be essentially constant indicating no corrosion. This was confirmed when the test was stopped and the copper coupon removed from the pipeline. The copper coupon showed no tarnish or corrosion.

Figure 7:
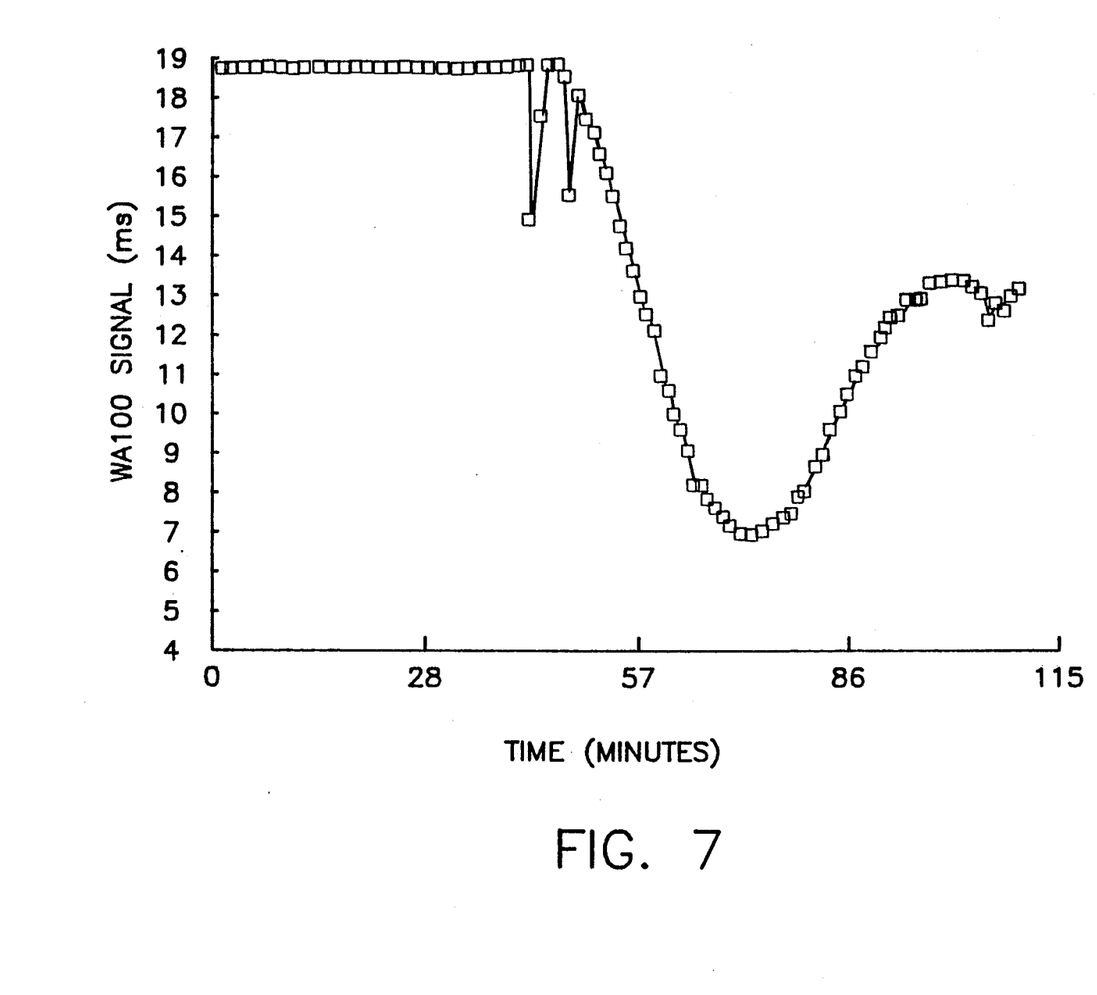
FIG. 7 shows how the present invention would alert a user of a major contamination within minutes.

In another test a coupon was exposed to a clean stream for three months and again showed no loss in reflectivity indicating no corrosion. At the end of the three months the product stream was intentionally contaminated with 10 ppm of hydrogen sulfide. The signal from the fiber optic probe during this part of the test is shown in FIG. 7. The signal from the fiber optic probe is seen to show the oscillatory behavior described in Example 1 indicating corrosion of the copper sample. After removal of the copper sample it was confirmed that the copper was corroded and the tarnish corresponded to an ASTM code of 2, again confirming the results of FIG. 2.

The utility of an on-line probe described by this invention may not necessarily be in assigning an ASTM code to a product stream in a pipeline since the test conditions are not according to the ASTM method. It is clear, however, that the slope of the reflectivity curve with time is related to the level of corrosive species in the product stream. More importantly and of immediate utility is the use of the invention to alert refinery operating personnel of major contaminations in the product stream.

In normal practice, a refinery typically runs the ASTM Copper Strip Corrosion Test once every eight hours on each pipeline. FIG. 7 clearly shows that the fiber optic corrosivity probe disclosed in this invention would alert the refinery within 15 minutes or less that a major contamination of the product stream had occurred.

The present invention has been described using examples primarily with liquefied petroleum gases. However, this is for illustration only and is not intended to limit the invention. The Copper Strip Corrosion Test is used with several other petroleum products such as Jet fuel, aviation fuel, gasoline and lubrication products and should find utility there as well.

We claim:

1. A method for on-line monitoring the corrosivity of a petroleum feedstream for the presence of a corrosive constituent comprising:
   (a) irradiating a metal that reacts with said corrosive constituent, said metal installed in said feedstream;
   (b) detecting the reflected radiation from said metal;
   (c) converting said reflected radiation to an electrical signal indicative of the magnitude of the reflected radiation;
   (d) repeating steps (a), (b), and (c) to give the change in reflectivity over a period of time;
   (e) determining a change in said electrical signal and relating it to the corrosivity of said feedstream of said metal from said reflectivity over a period of time.

2. The method of claim 1 wherein step (d) and step (e) are done continuously.

3. The method of claim 1 wherein said corrosive constituent includes sulfur or sulfur components.

4. The method of claim 1 wherein said metal includes copper.

5. A system for determining the presence of a corrosive constituent in a petroleum product comprising:
   (a) a housing having valves for admitting and releasing a sample of said petroleum feedstream;
   (b) a source of visible or infra-red light;
   (c) a metal that reacts with said corrosive constituent;
   (d) means for irradiating said metal with said light;
   (e) means for detecting the reflected light from said metal over a period of time;
   (f) means for converting said reflected light into an electrical signal over a period of time, the change of which is related to the corrosivity of said petroleum product.

6. The system of claim 5 wherein said means for converting gives a continuous signal.

7. The system of claim 5 further including a means to control the temperature of said housing.

8. The system of claim 5 wherein said means for irradiating and said means for detecting are fiber optics.

9. The system of claim 5 wherein said means for irradiating and said means for detecting are the same means.

10. The system of claim 5 wherein said metal is in the form of a metal thin film or metal coupon.

11. The system of claim 5 further comprising a strip chart recorder to record said electrical signals.

12. The system of claim 5 further comprising a computer having a data acquisition card to record said electrical signals.

* * * * *